US00PP08190P

United States Patent [19]

Holtkamp, Sr.

[11] Patent Number: Plant 8,190

[45] Date of Patent: Mar. 30, 1993

[54] AFRICAN VIOLET PLANT NAMED LITTLE COMANCHE GIRL

[76] Inventor: Reinhold Holtkamp, Sr., Blumenstrasse 28, D 4242 Rees-Haffen, Fed. Rep. of Germany

[21] Appl. No.: 736,640

[22] Filed: Jul. 26, 1991

[51] Int. Cl.[5] ..... A01H 5/00

[52] U.S. Cl. ..... Plt./69.2

[58] Field of Search ..... Plt./69.1, 69.2

*Primary Examiner*—James R. Feyer

*Attorney, Agent, or Firm*—Foley & Lardner

[57] ABSTRACT

A new and distinct cultivar of African violet named Little Comanche Girl characterized by its mid-size growth habit (13–15 cm in diameter); purplish blue, single violet-shaped flowers; strong stems which curve toward the center to form a compact bouquet above the leaves; profuse flowering; medium green, spear- to heart-shaped, slightly serrated leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar named Little Comanche Girl.

The new cultivar was referred to during the breeding and selection process by the designation 828/3 and is a product of a planned breeding program. The cultivar was originated from a cross made by me in the controlled breeding program in Haffen, Federal Republic of Germany. The female, or seed parent, was a cultivar designated 431/2. The male, or pollen parent, was a cultivar designated 528/3.

Little Comanche Girl was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Comanche Girl has not been observed under all possible environmental conditions. The phenotype may vary significantly with variations in environment such as temperature, light intensity and day length. The following observations, measurements and values describe the new cultivar as grown in a 5.5 cm pot in Haffen, West Germany and Nashville, Tenn. under greenhouse conditions which closely approximate those generally used in commercial practice.

The following traits have been repeatedly observed and are determined to be basic characteristics of Little Comanche Girl, which in combination distinguish this African violet as a new and distinct cultivar:

1) A single crown will not grow larger than 13–15 cm.

2) Single, purplish blue flowers.

3) Strong, wirelike and upright flower stems curving toward the center.

4) First flash of flowers forms a tight bouquet above the leaves.

5) Profuse flowering.

6) Each plant carries 6–8 and more upright flower stems each of which carries 5–6 and more flowers.

7) Long lasting, non-dropping flowers.

8) Plant saleable 10 to 11 weeks after planting of unrooted shoot.

9) Seed capsules push slightly through.

10) Medium green, hairy leaves.

11) Speak- to heart-shaped leaves are 3.0 to 4.0 cm in size.

12) After maturity the flowers dry off, and remain on the peduncle without becoming infected by botrytis.

The new cultivar is most similar to Little Navajo Girl, disclosed in U.S. Plant patent application Ser. No. 07/565,318. Similarities are the shape and color of the blossoms. However, Little Navajo Girl has Girl-type foliage and somewhat smaller blooms than Little Comanche Girl.

The accompanying color photographic drawing shows a typical specimen plant of the new cultivar grown in a 5.5 cm pot. The colors appearing in the photograph are as true as possible with color illustrations of this type.

In the following description, color references are made to the Royal Horticultural Society Colour Chart (R.H.S.), except where general colors of ordinary significance are referred to. Color values were taken under natural sunlight conditions at approximately 12 p.m. in Nashville, Tenn.

Botanical Classification: *Saintpaulia ionantha,* Ramat., c.v. Little Comanche Girl.

Parentage:

*Male parent.*—528/3.

*Female parent.*—431/2.

Propagation: The new cultivar holds its distinguishing charracteristics through successive propagations by leaf cuttings.

Plant: From 6 cm to 8 cm tall when grown in pots, and 13–15 cm in diameter when fully grown.

Leaves:

*General form.*—Spear- to heart-shaped.

*Diameter.*—30–34 mm wide and 35–38 mm long.

*Texture.*—Leatherlike.

*Aspect.*—Hairy, shiny, slightly serrated.

*Veins.*—Upperside: visible; underside: well pronounced, light green, shiny.

*Color (upperside).*—Yellow-Green Group 147 A.

*Color (underside).*—Greyed-Purple Group 186 A.

*Petiole.*—Strong, brownish green, hairy.

Flowers:

*Buds.*—Size: 5–6 mm just before opening. Shape: Bell-shaped. Color: Purplish blue.

*Sepals.*—Five (5). Color: Purplish brown.

*Calyx.*—Shape: Flat. Aspect: Spear-shaped, hairy.

*Peduncle.*—Character: Strong upright, hairy. Color: Brownish green.

Individual flowers:

*Size.*—32–36 mm.

*Shape.*—Single violet-shaped (3 large, 2 small petals).

*Color (upperside).*—Violet-Blue Group 93 between A and B. Under cooler temperatures and more intensive lighting, the purplish blue tends to intensify.

*Color (underside).*—Violet-Group 88 B.

*Borne.*—Each flower stem carries 5–6 and more flowers on strong, upright peduncles that are free standing above the leaves, thereby forming a compact bouquet.

*Flowering habit.*—Flowers 10–11 weeks after planting an unrooted plantlet.

Reproductive organs:

*Stamens.*—Two (2). Anthers: 2 composed of 4 anther cells, seed capsule pushes slightly through.

*Filaments.*—Yellowish green, 3–4 mm long.

*Styles.*—5–6 mm long, purplish blue, base of ovary light green and hairy.

Roots: Normally developed, white when young, turning slightly brownish when older.

Disease resistance: Up to date, Little Comanche Girl has shown very good resistance to all major violet diseases.

General observations:

Little Comanche Girl is a mid-size violet, a size between a regular violet (grown in a 10 cm pot) and a superminiature (grown in a 4 cm pot). Little Comanche Girl is designed to be grown in a 5.5 cm to 6 cm pot and will not grow larger than 13–15 cm. It is very attractive due to its purplish blue flowers contrasting nicely with the bright yellow anthers. A nice bouquet of flowers free standing above the leaves develops 10–11 weeks after planting an unrooted plantlet. Each of the 6–8 and more strong flower stems carries 5–6 and more single violet-shaped flowers. The flowers are long-lasting and non-dropping. The medium green leaves are spear- to heart-shaped and slightly serrated.

I claim:

1. A new and distinct cultivar of African violet named Little Comanche Girl, as described and illustrated, and particularly characterized by its mid-size growth habit (13–15 cm in diameter); purplish blue, single violet-shaped flowers; strong stems which curve toward the center to form a compact bouquet above the leaves; profuse flowering; medium green, spear- to heart-shaped, slightly serrated leaves; flowering 10–11 weeks after planting of unrooted shoot, and by its long lasting and non-dropping flowers.

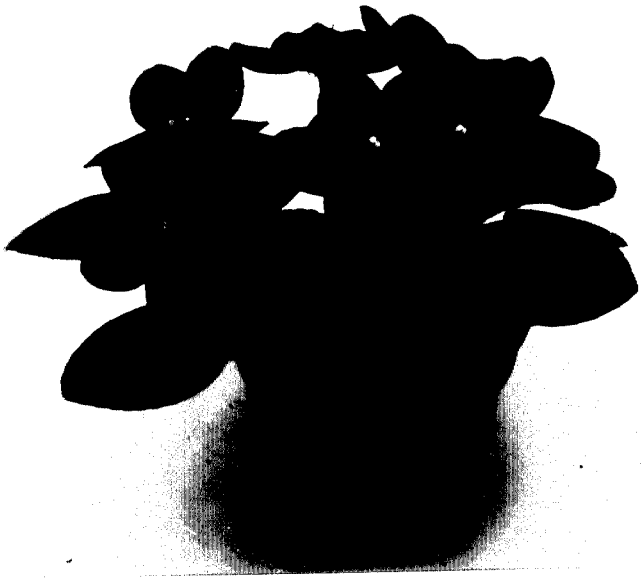

* * * * *